(12) United States Patent
Hu

(10) Patent No.: US 8,967,163 B2
(45) Date of Patent: Mar. 3, 2015

(54) TEETH CLEANING DEVICE

(71) Applicant: Kun Hu, West Covina, CA (US)

(72) Inventor: Kun Hu, West Covina, CA (US)

(73) Assignee: Jetpik, City of Industry, CA (US)

(*) Notice: Subject to any disclaimer, the term of this patent is extended or adjusted under 35 U.S.C. 154(b) by 65 days.

(21) Appl. No.: 13/895,530

(22) Filed: May 16, 2013

(65) Prior Publication Data

US 2014/0373866 A1    Dec. 25, 2014

(30) Foreign Application Priority Data

Jan. 17, 2013    (CN) .......................... 2013 1 0018572

(51) Int. Cl.
| A61C 15/00 | (2006.01) |
| A45D 44/18 | (2006.01) |
| A61C 17/02 | (2006.01) |
| A61C 15/04 | (2006.01) |

(52) U.S. Cl.
CPC ............. *A61C 17/0202* (2013.01); *A61C 15/00* (2013.01); *A61C 15/047* (2013.01)
USPC ........................................ 132/322; 132/309

(58) Field of Classification Search
CPC .... A61C 15/00; A61C 15/046; A61C 15/047; A61C 17/0214; A61C 17/0202; A46B 2200/108
USPC .......... 132/321–329, 309; 433/80, 84, 85, 87, 433/89, 90, 99, 100, 118, 82, 88; 601/160–165, 169; 15/22.1, 22.2
See application file for complete search history.

(56) References Cited

U.S. PATENT DOCUMENTS

| 3,472,247 | A | * | 10/1969 | Borsum et al. ................. 132/322 |
| 4,031,908 | A | * | 6/1977 | Ting ............................... 132/322 |
| 4,326,549 | A | * | 4/1982 | Hinding ......................... 132/322 |
| 5,027,798 | A | * | 7/1991 | Primiano ....................... 601/165 |
| 5,183,065 | A | * | 2/1993 | Mason ........................... 132/323 |
| 5,570,709 | A | * | 11/1996 | Haddad et al. ................ 132/322 |
| 5,709,233 | A | * | 1/1998 | Boland et al. ................. 132/322 |
| 5,769,102 | A | * | 6/1998 | Zebuhr .......................... 132/322 |
| 5,906,213 | A | * | 5/1999 | Diffendal ...................... 132/309 |
| 6,193,512 | B1 | * | 2/2001 | Wallace ........................... 433/80 |
| 6,526,994 | B1 | * | 3/2003 | Santoro ......................... 132/322 |
| 6,689,078 | B1 | * | 2/2004 | Rehkemper et al. .......... 601/162 |
| 6,740,053 | B2 | * | 5/2004 | Kaplowitz ..................... 601/162 |
| 2001/0034006 | A1 | * | 10/2001 | Lang et al. ..................... 433/118 |
| 2008/0092917 | A1 | * | 4/2008 | Getgey et al. ................. 132/322 |
| 2008/0289648 | A1 | * | 11/2008 | Liu ................................. 132/322 |
| 2011/0262879 | A1 | * | 10/2011 | Hegemann ...................... 433/82 |

* cited by examiner

*Primary Examiner* — Vanitha Elgart
(74) *Attorney, Agent, or Firm* — Jen-Feng Lee, Esq.

(57) ABSTRACT

A teeth cleaning device with a core pump area that provides positive pressure to push out water jetting streams and negative pressure to retract the floss attached to a piston, while the power input has enhanced torque due to the bevel gear structure; an optional spring may be placed inside the piston assembly to add to the reciprocating power, and thus creating more effective water jetting and floss oscillating motions for better teeth cleaning.

9 Claims, 4 Drawing Sheets

TEETH CLEANING DEVICE

RELATIONSHIP TO OTHER FILING AND PRIORITY CLAIM

This application claims the foreign priority filing date of Jan. 17, 2013, application number 201310018572.8, pursuant to 35 USC §119.

FIELD AND BACKGROUND OF THE INVENTION

The present invention relates generally to a teeth cleaning device.

There are numerous little gaps in between human teeth. To effectively clean the surface and the gaps has always been a challenge to consumers in their everyday lives. Since not all teeth are born or maintained to have uniformly regular shapes, the task of effective cleaning is made even more difficult.

Though many traditional manual tools are available, such as spools of floss, and floss made onto a small toothpick type stick for easy holding, they do not achieve an ideal level of desired teeth cleaning effect. Electrically-powered and water-jetting based tools became popular.

One popular type of water jetting teeth cleaning device consist of a spray nozzle 1, a water pump 2, water inlet 8 on said nozzle, water outlet 9 on said water pump. A reciprocating piston inside said water pump causes water to go into spray nozzle 1 and produces pulsating water jet streams to come out of the nozzle's external end.

A brush tip 5 (or a short length of a floss) is connecting to a piston 6 rested in the junction area of said nozzle, so that when the brush tip 5 is pushed out (by the pulsating water jets), it will be retracted back in by a spring 7 inside said nozzle.

The oscillating/reciprocating function of the brush tip 5 (or a floss tip) helps to achieve the cleaning on the surface of the teeth.

Reference prior art drawings in FIGS. 1 & 2.

This type of simple design depends on the "positive" pressure going from the pump 2 towards the nozzle 1. Due to the inherent nature of the spring's resilient force, the brush tip's action, especially at the stage where the brush tip is nearly extended out of the nozzle tip, where the pulsating water pressure is at its lowest and the spring's resilient force is at its strongest, the brushing/cleaning power is weakened, due to the "mutual cancellation" effect inherent in this type of design.

To overcome the "weaker" retraction action of the brush tip, some devices employ higher water pumping pressure. Though simple to do so, another downside quickly shows: the spring is unable to provide its full retracting force, so as to result in full range travel of the brush tip.

As such, the brush tip's cleaning power to reach into tooth gaps is quite limited.

In light of such "mutual cancellation" problem, present invention uses a one-way valve actuated by a transmission device to produce negative pressure that produces the retraction force of the brush tip (or floss line), thus providing fuller travel of the brush tip (or floss line) and stronger-torqued reciprocating piston motions (use of bevel gears for speed reduction and torque enhancement), resulting in more effective teeth cleaning water-jetting and back-and-forth flossing movement, even if the source of the water pump is at the same power output level as the traditional device.

A spring can optionally be placed inside piston connection assembly, around a piston rod, to help with the back-and-forth oscillating action of the tube piston, which drives the flossing tip's motion.

The modular design of present invention allows different materials of floss to be affixed to the floss holding component, to work on different surface of teeth and gaps between teeth, as the users prefer. By the use of the reciprocating water jetting streams, at exemplary frequency of 30 Hz, the effective cleaning function achieved by the design of present invention will exceed that of the traditional simple water-jetting devices.

DETAILED DESCRIPTION OF PREFERRED EMBODIMENT

Figure 1:
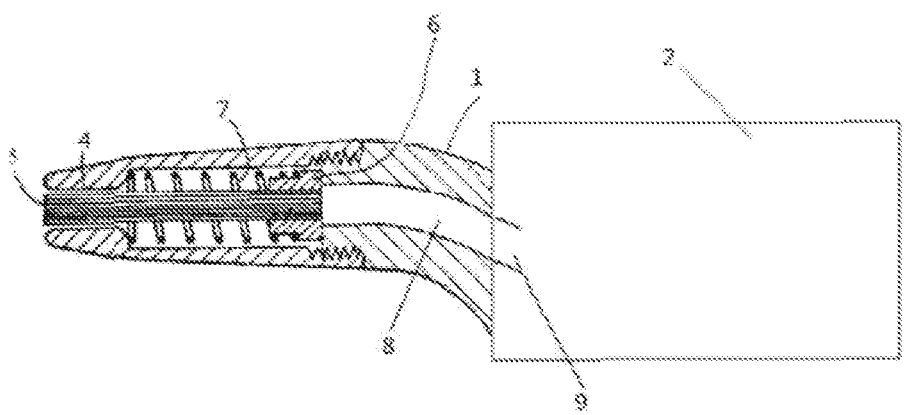
FIG. 1 shows prior art construction of a teeth cleaning device with simple water jetting streams shot out by a motor unit attached inside a handle portion.
Figure 2:
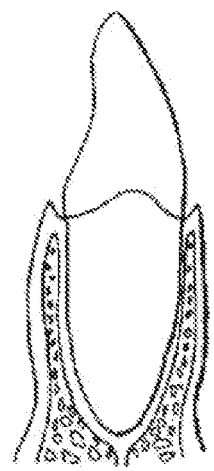
FIG. 2 shows the profile of a tooth for the intended location of water jetting streams' contact when using a teeth cleaning device.

The teeth cleaning device of present invention mainly consists of a piston connection assembly 303 inside a long tube 302, for connecting to a handle head portion of the device, where external water port 390 is connected to and fed into the handle portion, and is further pumped into the device of present invention in pulsating streams.

At the handle head portion of a handle, there are two major components to work with said piston connection assembly 303 of present invention: a pump core area 301 and a transmission device 319 inside said handle portion to transform the rotary power into the needed reciprocal actions, with torque enhancement mechanism, as discussed later.

Figure 3:
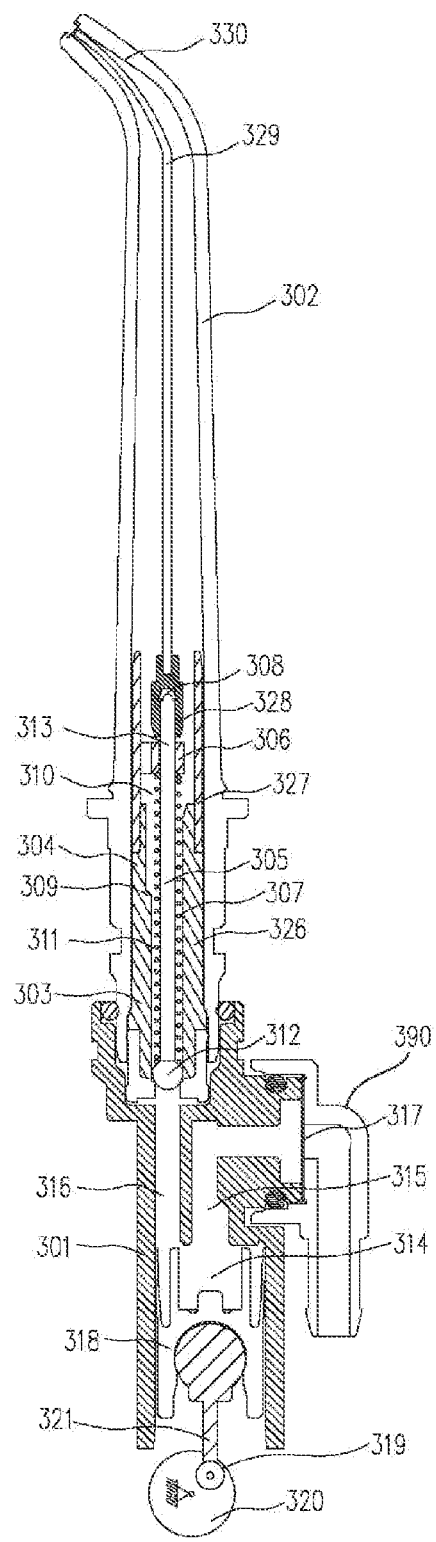
FIG. 3 shows the implementation of a teeth cleaning device according to the disclosure of present application, with an optional spring.
Figure 4:
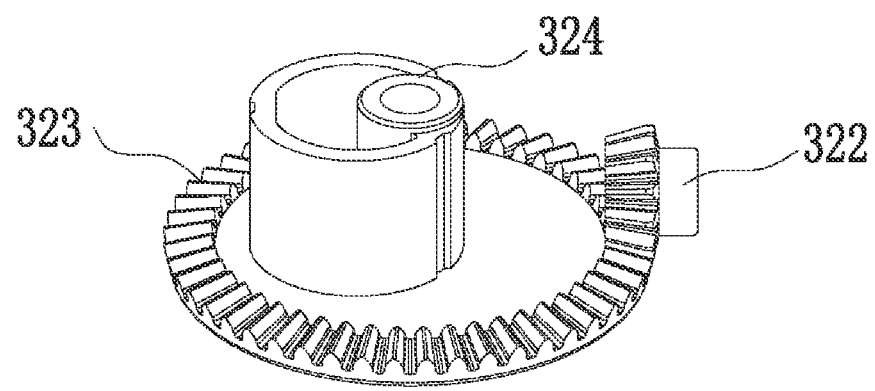
FIG. 4 shows the transmission device for converting the motor-driven circular motion to reciprocating actions of the piston that is used in present application.
Figure 5:
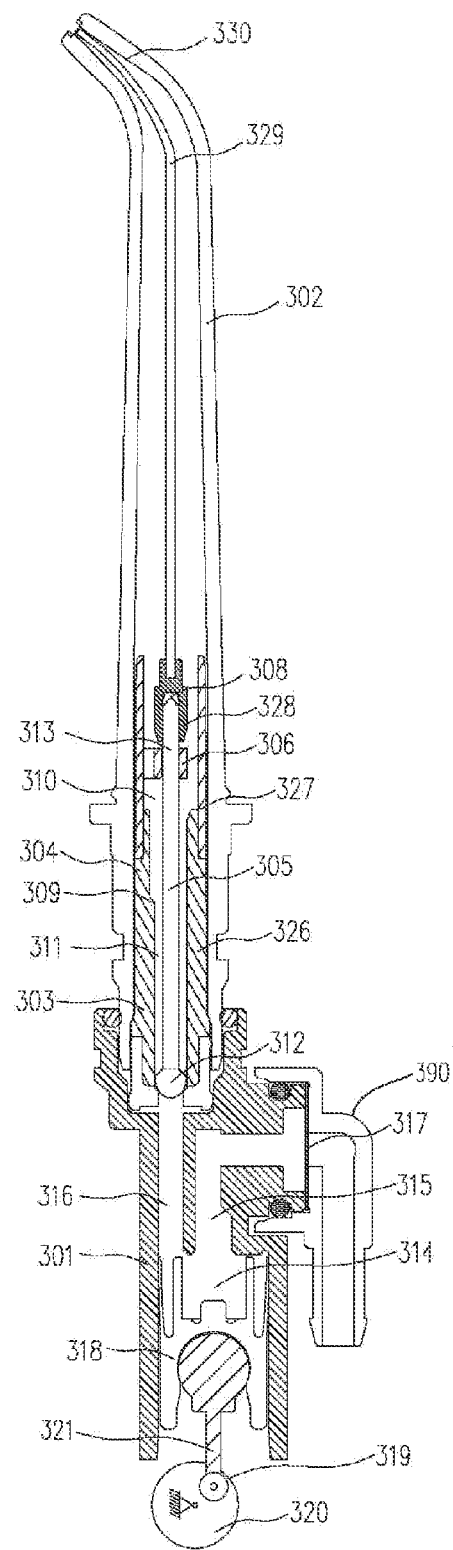
FIG. 5 shows the implementation of a teeth cleaning device without the use of a spring.

Refer to FIGS. 3, 4 and 5 for the components and parts and the structural implementation discussed herein.

Said pump core area 301 consists of an inlet passage 315, transit chamber 314 and an outlet passage 316. A one-way valve 317 sits at the junction between said inlet passage 315 and the external water port 390, so as to control and allow only one-way action of water coming into said pump core area 301. Said one-way valve 317 also serves to provide a "negative pressure" for the intended function, as further explained below.

For ease of reference and understanding, a "positive" water pressure represents the water pressure direction where the water is moving from the handle portion towards the long tube 302 and towards a nozzle 330 portion. Consequently, a "negative" pressure represents the scenario where the water tends to flow from the long tube 302 towards the handle portion and the transit chamber 314.

A main piston 318 moves back-and-forth to push the water from inside said inlet passage 315 and towards said outlet passage 316, and onward to said long tube 302 via piston connection assembly 303.

Said main piston 318 will be driven by said transmission device 319 comprising of a small bevel gear 322, a large bevel gear 323, a connector seat 324 and a connecting rod 321.

A motor 320 drives said small bevel gear 322, which then drives said large bevel gear 323. Refer to the FIG. 4 to see the physical engagement between said two bevel gears 322/323, where the output speed (of the large bevel gear) will be reduced and the torque power will be enhanced, due to the setup of a small bevel gear driving a large bevel gear.

Said connector seat 324 will be made onto the planar surface of said big bevel gear 323. An exemplary implementation would be to mold said connector seat 324 to said large bevel gear 323.

Said connector rod 321 (shown on FIGS. 3 and 5) will transform the rotary action of said big bevel gear 323 into linear reciprocal actions (back-and-forth) to push/pull said main piston 318, much like the way a car engine piston works inside a cylinder.

Said piston connection assembly 303 is located inside said long tube 302, and contains an outer shell 304, a tube piston 305, a holding rack 306, an optional spring 307 and a floss holding component 308.

Said outer shell 304 provides for an internal piston chamber area and may be made up of two parts: a piston shell 326 and a flood shell 327.

In the internal piston chamber area defined by said outer shell 304, a flood step 309 is made as a separating point for two segments: flood passage 310 and piston passage 311. The diameter of flood passage 310 is bigger than that of the piston passage 311.

Due to the design of the present invention, the system produces alternating "positive" and "negative" pressures, causing the tube piston 305 to be driven forward (with positive pressure) and backward (with negative pressure), resulting in the desired back-and-forth action of the flossing motions.

An optional spring 307 may be placed around said tube piston 305, inside the space of said outer shell 304, further assisting the initialization position of the tube piston 305 and its oscillating motion.

Said outer shell 304 wraps around the floss holding component 308, the optional spring 307, the holding rack 306 and the tube piston 305, along the longitudinal direction of the long tube 302.

Said tube piston 305 further consists of a piston head 312 and a piston rod 313. Said piston head 312 is slidably engaged to inner surface of said piston passage 311 and will be moving back-and-forth by the push and pull action produced when the main piston 318 drives the water jet streams in a pulsating manner.

One end of said spring 307, when optionally set, will be connecting to said holding rack 306 and the other end will be connecting to the piston head 312 of said tube piston 305.

Said holding rack 306 serves to hold the piston rod 313 which is slidably engaged with holding rack 306 while being pushed back-and-forth by main piston 318. The holding rack 306 may be implemented as a ring structure inside said outer shell 304; particularly, it may be made to anchored on the inside surface of said flood shell 327.

The floss holding component 308 connects to a distal end of said piston rod 313 when a string of floss 329 extends from said floss holding component 308 through the inner space of said long tube 302 and towards a nozzle 330 portion of said long tube 302.

Said nozzle 330 may be tapered at the distal end and it may also be made to bent an angle, as shown in FIG. 3.

The floss holding component 308 further contains a floss sheath 328 to hold the floss string 329.

The back-and-forth action of main piston 318 has two positions worth discussing herein. A far-rest point is the location where said main piston 318 is closest to said transit chamber 314. A near-rest point is the location where main piston 318 is closest to said transmission device 319.

The present invention allows the removable modular design for the long tube 302 and the piston connection assembly 303 (which sits inside said long tube 302), so that the whole piston connection assembly 303 can be taken out from said long tube 302, and the long tube 302 can be removed from said handle portion, for ease of cleaning or replacement.

Such modular design also allows the variation of effective flossing length by the extent of floss 329 extending out of the nozzle 330 (and back, in a reciprocating action), by changing the length of flood passage 310, or setting a different position for the flood step 309.

When said main piston 318 is at the far-rest point, it cuts off the water flow connection between inlet passage 315 and outlet passage 316. When said main piston 318 is at the near-rest point, the water flow between said inlet passage 315, outlet passage 316 and transition chamber 314 is enabled.

Said motor 320 may further has power control circuitry that allows user to effect control of output power, either in steps or sliding stepless fashion.

Said motion 320 can be driven by a battery on board the handle portion, or have direct corded power supply, depending on the cost and other design factors.

The following paragraphs briefly explain the cycle of push-pullback action of the main piston 318 to produce a jet stream of water.

When main piston 318 moves from the far-rest point towards the near-rest point, said piston head 312 will close the connection between long tube 312 and pump core area 301, and a negative pressure is formed inside said transition chamber 314. Consequently, one-way valve 317 will open (towards inlet passage 315) and allow water from the external water port 390 to be suctioned through said inlet passage 315 and placed to said transition chamber 314.

When main piston 318 moves from the near-rest point towards the far-rest point, the one-say valve 317 will be closed, the water suctioned into the pump core area 301 will travel through said outlet passage 316 and towards the long tube 302.

When the main piston 318 moves towards the far-rest point, said piston head 312 will move, along the water pressure direction, towards said flood step 309. As such, the streams of water move from said piston passage 311 towards said flood passage 310, the latter of which has bigger inner diameter than the former. The water continues to move towards the nozzle 330 and shots out to form a jetted stream.

Said piston head 312 drives said piston rod 313, whose distal end contains the floss holding component 308 that includes a string of floss 329 that can be push out of said nozzle 330, achieving an in-and-out (of the nozzle 330) action.

When the out-traveling water pressure dissipates, the negative pressure, plus the optional spring 307, will cause said piston head 312 to restore back to its original position. After said piston head 312 travels back through the point of flood step 309, the water connection between the pump core area 301 and long tube 302 will be closed off, completing shutting off any water pressure towards the tube/nozzle direction. This is the end of a push-pull back cycle of the main piston 318.

What is claimed is:

1. A teeth cleaning device, comprising:
a handle head portion, further comprising a transmission device and a pump core area consisting of an outlet passage, an inlet passage and a transit chamber, with a one-way valve situated between said inlet passage and an external water port, allowing water to be delivered into said pump core area;
a long tube connected to said handle head portion, said long tube further having a tapered nozzle at a distal end, and;
a piston connection assembly inside said long tube, further comprising a floss holding component, a holding rack, a tube piston and an outer shell to wrap around said floss holding component, holding rack and tube piston, along the longitudinal direction of said long tube.

2. The teeth cleaning device of claim 1, wherein said tube piston is made up by a piston head and a piston rod.

3. The teeth cleaning device of claim 2, wherein said piston rod is slidably engaged by said holding rack, and will move said floss holding component back and forth by the water pressures produced by said pump core area.

4. The teeth cleaning device of claim 3, wherein said outer shell is made up of two segments, with a piston shell segment being closer to said handle head portion and a flood shell segment being closer to said nozzle.

5. The teeth cleaning device of claim 4, wherein said transmission device further comprising a connecting rod, a small bevel gear, a large bevel gear and a connector seat whereby the rotational power sent from a motor causes said small bevel gear to drive said large bevel gear, and said connector seat causes the connecting rod to move in a reciprocal fashion to move a main piston situated inside said handle head portion.

6. The teeth cleaning device of claim 5, wherein an optional spring may be placed around said tube piston inside the space of said outer shell, providing assisting reciprocating power to provide oscillating motions.

7. The teeth cleaning device of claim 5, wherein a flood step is formed at the junction of said piston shell segment and said flood shell segment, resulting in a piston passage and a flood passage, said piston passage being closer to said handle head portion and is narrower in diameter than that of said flood passage.

8. The teeth cleaning device of claim 5, wherein said floss holding component further comprising a floss sheath to hold a string of floss.

9. The teeth cleaning device of claim 5, wherein said holding rack may be a ring structure inside said outer shell.

* * * * *